(12) United States Patent
Pratt et al.

(10) Patent No.: US 9,249,890 B2
(45) Date of Patent: Feb. 2, 2016

(54) FITTINGLESS PNEUMATIC MULTIPORT SELECTOR VALVE FOR ANALYTIC INSTRUMENTS

(71) Applicant: Rosemount Analytical Inc., Houston, TX (US)

(72) Inventors: Jason P. Pratt, Cypress, TX (US); Shane Hale, Jersey Village, TX (US); Willis Watkins, Cypress, TX (US)

(73) Assignee: Rosemount Analytical Inc., Houston, TX (US)

( * ) Notice: Subject to any disclaimer, the term of this patent is extended or adjusted under 35 U.S.C. 154(b) by 342 days.

(21) Appl. No.: 13/826,569

(22) Filed: Mar. 14, 2013

(65) Prior Publication Data

US 2014/0260538 A1 Sep. 18, 2014

(51) Int. Cl.
| | |
|---|---|
| *G01N 30/04* | (2006.01) |
| *G01N 30/02* | (2006.01) |
| *G01N 30/90* | (2006.01) |
| *B01D 53/02* | (2006.01) |
| *B01D 53/14* | (2006.01) |
| *F16K 11/00* | (2006.01) |
| *G01N 30/32* | (2006.01) |

(52) U.S. Cl.
CPC ............... *F16K 11/00* (2013.01); *G01N 30/32* (2013.01); *G01N 2030/328* (2013.01); *Y10T 137/86879* (2015.04)

(58) Field of Classification Search
None
See application file for complete search history.

(56) References Cited

U.S. PATENT DOCUMENTS

| | | | | |
|---|---|---|---|---|
| 3,535,939 | A * | 10/1970 | Dobbs et al. | 251/62 |
| 4,133,640 | A * | 1/1979 | Clinton | G01N 30/30 |
| | | | | 422/78 |
| 4,276,907 | A * | 7/1981 | Broerman | 137/637.2 |
| 5,601,115 | A * | 2/1997 | Broerman | 137/595 |
| 6,202,698 | B1 * | 3/2001 | Stearns | 137/627.5 |
| 6,374,860 | B2 * | 4/2002 | Xu et al. | 137/884 |
| 7,216,528 | B2 * | 5/2007 | Gamache et al. | 73/23.41 |
| 7,584,675 | B2 * | 9/2009 | Evans | 73/863.41 |
| 8,104,506 | B2 * | 1/2012 | Gamache et al. | 137/597 |
| 8,418,526 | B2 * | 4/2013 | He et al. | 73/19.01 |
| 8,434,512 | B2 * | 5/2013 | Bergmann et al. | 137/625.18 |
| 8,794,594 | B2 * | 8/2014 | Gamache et al. | 251/331 |
| 8,851,452 | B2 * | 10/2014 | Gamache et al. | 251/335.2 |

* cited by examiner

*Primary Examiner* — Peter Macchiarolo
*Assistant Examiner* — Jermaine Jenkins
(74) *Attorney, Agent, or Firm* — Christopher R. Christenson; Kelly, Holt & Christenson, PLLC

(57) ABSTRACT

A pneumatic multiport selector valve and analytic instrument employing said valve are provided. The valve includes a base having a mounting surface configured to mount to the analytic instrument. The mounting surface has a plurality of apertures therein for coupling to flow conduits of the analytic instrument. At least one piston plate has a number of apertures therethrough. The apertures are configured to slidably receive respective pistons. Pistons are disposed in respective apertures of the at least one piston plate. A cushion layer is disposed between the at least one piston plate and the base. The cushion layer has a plurality of apertures to allow actuation gas therethrough. A plate clamps the at least one piston plate to the base.

15 Claims, 6 Drawing Sheets

FITTINGLESS PNEUMATIC MULTIPORT SELECTOR VALVE FOR ANALYTIC INSTRUMENTS

BACKGROUND

Analytic instruments are used in a number of applications to quantitatively and/or qualitatively analyze a sample of interest. Analytic instruments are often found in laboratories and are sometimes employed within processing operations. As used herein, an analytic instrument is any device, system or arrangement that is able to receive a sample of interest and provide an indication of some aspect of the sample of interest. Analytic instruments include, without limitation, process gas analyzers, NO/NOx analyzers, hydrocarbon analyzers, continuous emission monitoring systems and process gas chromatographs.

A variety of analytic instruments employ regulated flows and a number of flow paths in order to provide analyses regarding various chemicals in processing or analytic contexts. The analytic instruments typically function using one or more flow devices that can initiate, interrupt, and reverse flow through the device. Such variety of flow functions is usually provided by a combination of one or more flow valves and/or pumps. In order to function effectively, analytic instruments will generally include a plurality of sample flow paths. In the context of a gas chromatograph, a number of flow paths are used to introduce a flow of sample and carrier gas into the gas chromatograph; flow a controlled amount of sample across a sorbent column; reverse the flow to elute the sample from the column; and detect the various components in the flow stream.

Gas chromatographs generally use pneumatic multiport valves to switch the flow of gas during analysis. These valves are critical to establishing a flow which allows the gasses to be separated. Among other things, it is very important that the gasses be able to enter and exit the valve with low leakage. This has been accomplished in the past through tube fitting connections or other various means. It is common for multiport flow selector valves to have 6 or even 10 individual ports, in addition to the actuation gas ports required for pneumatic actuation. A gas chromatograph may employ a number of such multiport selector valves. Accordingly, the time required to couple each tube to its respective port can add up to significant assembly time. Further, each individual tube connection is subject to variations in operator torque, tubing modifications, such as bending or routing, et cetera.

As the art of process analytic devices has progressed, there is increasing pressure to provide a lower-cost, higher-performance analytic instrument.

SUMMARY

A pneumatic multiport selector valve and analytic instrument employing said valve are provided. The valve includes a base having a mounting surface configured to mount to the analytic instrument. The mounting surface has a plurality of apertures therein for coupling to flow conduits of the analytic instrument. At least one piston plate has a number of apertures therethrough. The apertures are configured to slidably receive respective pistons. Pistons are disposed in respective apertures of the at least one piston plate. A cushion layer is disposed between at least one piston plate and the base. The cushion layer has a plurality of apertures to allow actuation gas therethrough. A plate clamps at least one piston plate to the base.

DETAILED DESCRIPTION OF ILLUSTRATIVE EMBODIMENTS

Figure 1:
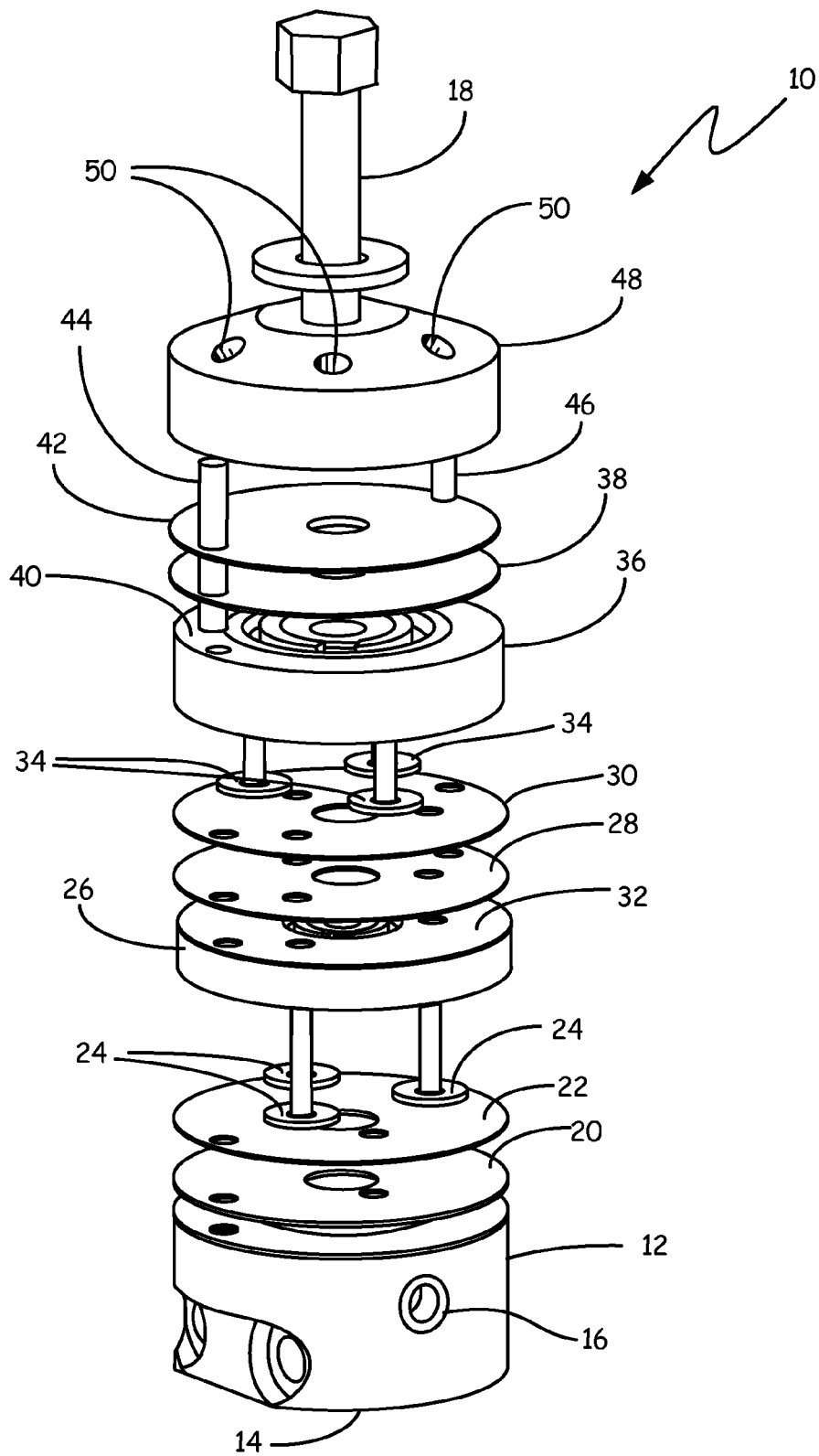
FIG. 1 is a diagrammatic exploded view of a multiport flow selector valve in accordance with the prior art.

FIG. 1 is a diagrammatic exploded view of a multiport flow selector valve in accordance with the prior art. Valve 10 includes base plate 12 that has a mounting surface 14 that couples to an analytic instrument, such as a gas chromatograph. Base plate 12 includes a plurality of pneumatic actuation ports 16 that couple to a suitable source of actuation gas, such as carrier gas, compressed air or nitrogen. Base plate 12 includes a through-hole in its center allowing bolt 18 to pass therethrough in order to supply the force to clamp the components of valve 10 together. The base plate 12 includes a plurality of horizontal holes used exclusively for mounting the valve 10 to the analytic instrument.

Layers 20 and 22 comprise a lower actuator diaphragm and are generally formed of polyimide such as that sold under the trade designation Kapton® available from E. I. du Pont de Nemours and Company of Wilmington, Del. Three long pistons 24 are disposed proximate lower actuator diaphragm 22 and slidably extend into lower piston plate 26. Upper actuator diaphragm layers 28, 30 are preferably formed of polyimide and are disposed proximate surface 32 of lower piston plate 26. Pistons 34 are positioned proximate diaphragm layer 30 and slidably extend into upper piston plate 36. A cushion layer 38 is formed of a material that can absorb and/or attenuate at least some physical motion. For example, cushion layer 38 can be formed of a meta-aramid material such as that sold under the trade designation, Nomex® available from E. I. du Pont de Nemours and Company. Cushion layer 38 is disposed proximate surface 40 of upper piston plate and a sealing diaphragm 42 is disposed proximate cushion layer 38.

A pair of alignment pins 44, 46 extends into primary plate 48 and through layers 42, 38, 30, 28, 22, 20 as well as through plates 36, 26. Alignment pins 44, 46 help maintain careful positioning of the various components of valve 10 during assembly.

Primary plate 48 provides the ports of the multi-port valve 10. The ports are indicated at reference numeral 50 and are generally internally threaded to accept standard tube fittings. Once valve 10 is fully assembled and mounted into the gas chromatograph, it is necessary to attach tubing to the individual ports and the pneumatic control line ports. For a gas chromatograph having three such multiport selector valves, the assembly process is complex and labor intensive. Moreover, if a valve needs to be replaced, all of the discrete tubing connections for that valve must be removed and the valve must be unbolted from the gas chromatograph. When the valve is repaired, rebuilt or otherwise replaced, the entire assembly must generally be recalibrated to account for any minor variations introduced with the new/repaired valve.

Figure 2:
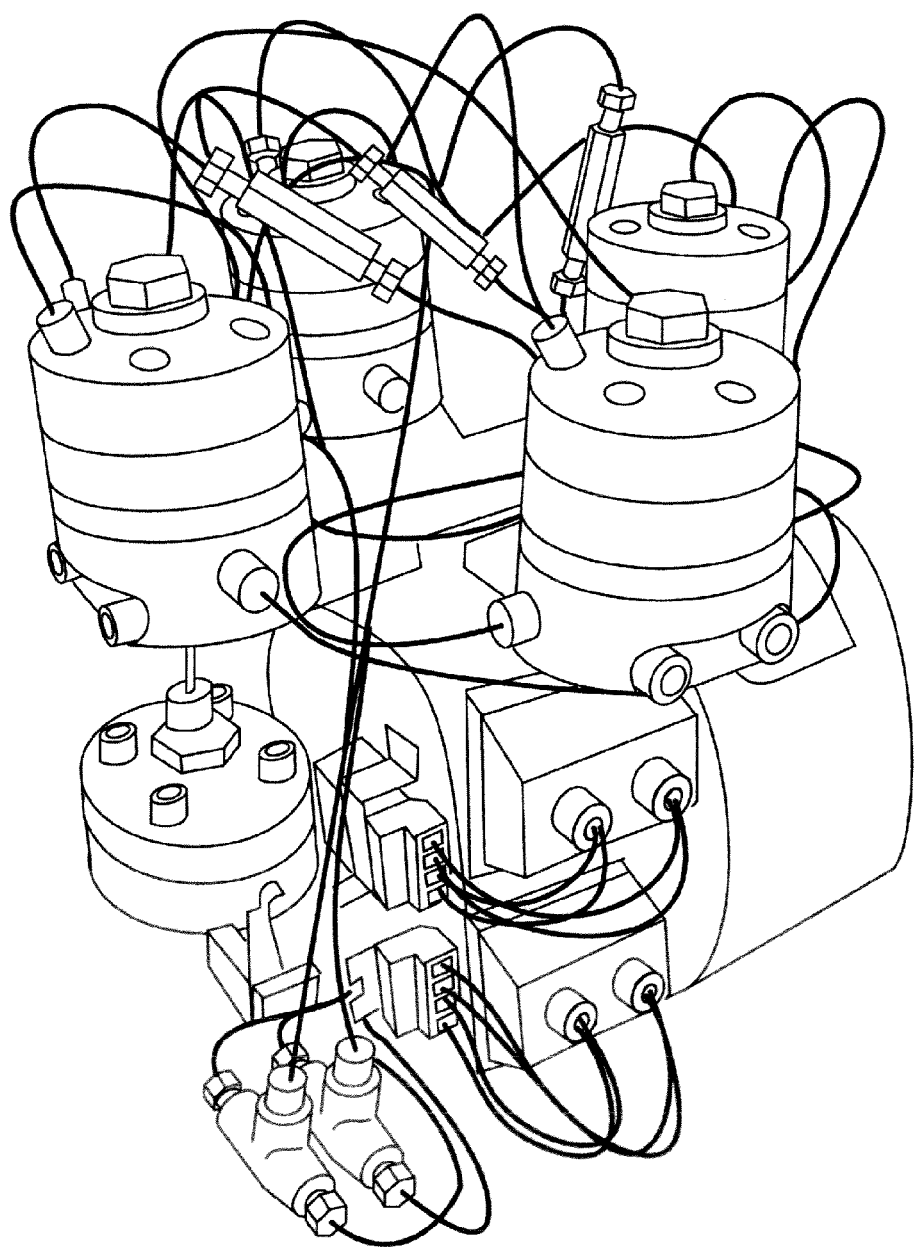
FIG. 2 is a diagrammatic view of a portion of a gas chromatograph employing multiport selector valves in accordance with the prior art.

FIG. 2 is a diagrammatic view of a portion of a gas chromatograph employing multiport selector valves in accordance with the prior art. As illustrated, there are a significant number of tubing connections made on the top of each multiport selector valve along with a significant number of tubing bends.

Figure 3:
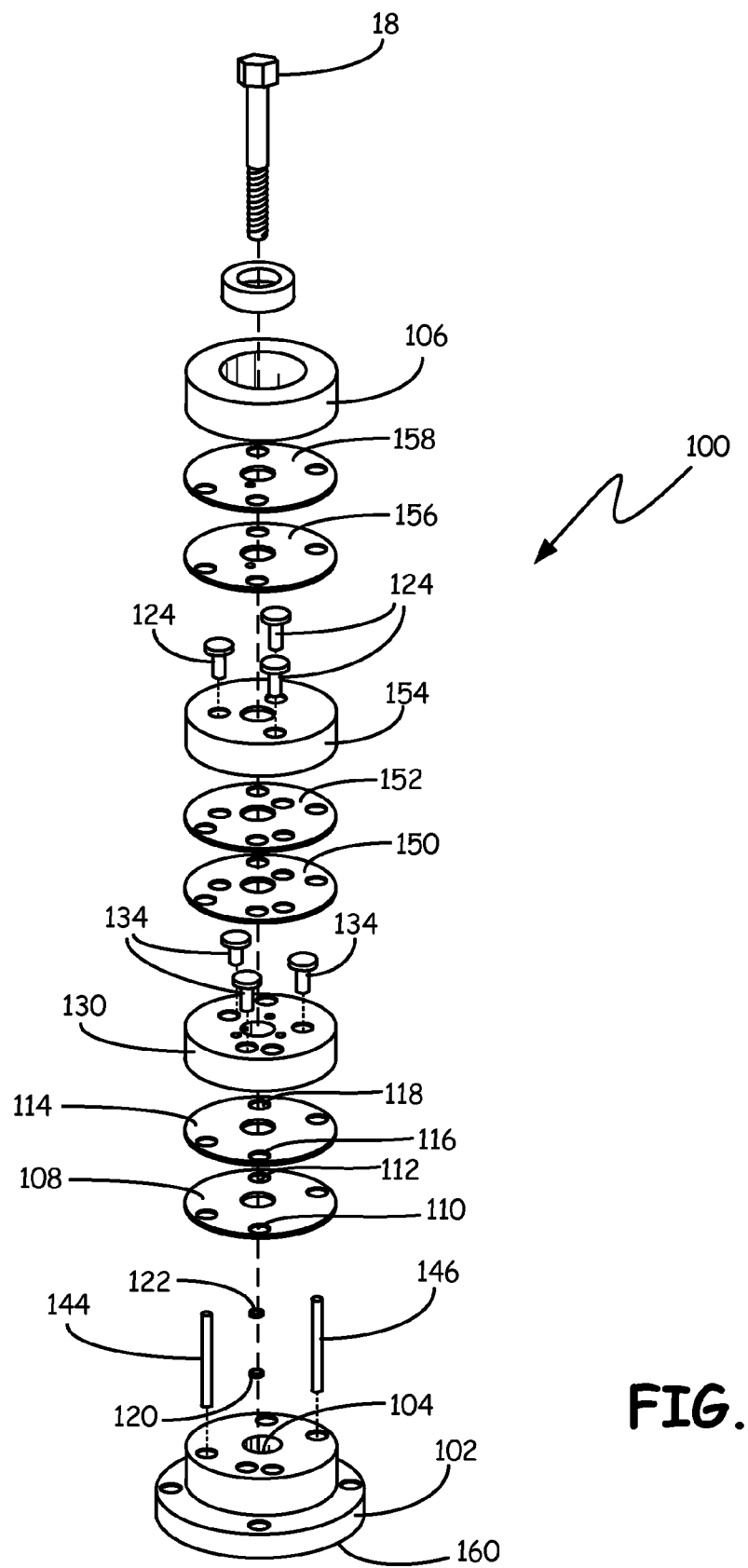
FIG. 3 is a diagrammatic exploded view of a multiport selector valve in accordance with an embodiment of the present invention.

FIG. 3 is a diagrammatic exploded view of a multiport selector valve in accordance with an embodiment of the present invention. Valve 100 includes base plate 102 which is substantially different than base plate 12 of valve 10. Valve 100 includes an internally threaded bore 104 in its center that mates with threads of bolt 18. Guide pins 144 and 146 extend into base plate 102 and through all other layers of valve 100 into plate 106. Seal layer 108 is disposed proximate base plate 102 and includes a pair of apertures 110, 112 (in addition to the alignment apertures and the center aperture) that allow actuation gas to pass therethrough. Seal layer 108, in one embodiment, may be formed of polyimide. Similarly cushion layer 114 includes a pair of apertures 116, 118 to allow actuation gas to pass therethrough. Cushion layer 114 is preferably formed of a meta-aramid material such as Nomex®. However, given the porous nature of this meta-aramid material, it is important to isolate it from the actuation gas. Thus, a pair of o-rings 120, 122 is clamped between base plate 102 and first piston plate 130 within respective apertures 110, 116 and 112, 118 in layers 108 and 114. O-rings 120, 122 ensure that actuation gas flowing into first piston plate 130 from base plate 102 will not contact cushion layer 114.

A first set of pistons 134 is slidably received within first piston plate 130. A pair of actuator diaphragm layers 150, 152 is disposed between first piston plate 130 and second piston plate 154. Layers 150, 152 are preferably formed of polyimide and include apertures for alignment pins 144, 146; pistons 124; actuation gas; and bolt 18. A second set of pistons 124 is slidably received within second piston plate 154. A second pair of actuation diaphragm layers 156, 158 is positioned between second piston plate 154 and plate 106. Layers 156, 158 are also preferably formed of polyimide.

Plate 106, unlike plate 48 (shown in FIG. 1) is devoid of any tubing ports. Instead, fluidic connections to valve 100 are made via mounting surface 160 on base plate 102. Surface 160 includes a plurality of apertures. Each port of multiport valve 100 has an aperture in surface 160 that aligns with and is coupled to a fluidic connection or port in the gas chromatograph (illustrated in FIG. 5). Further, fluidic connections for actuation gas are also done via apertures in surface 160. Moreover, given the planar nature of surface 160, all of the fluidic connections can be made simultaneously as valve 100 is clamped into the gas chromatograph.

Figure 4:
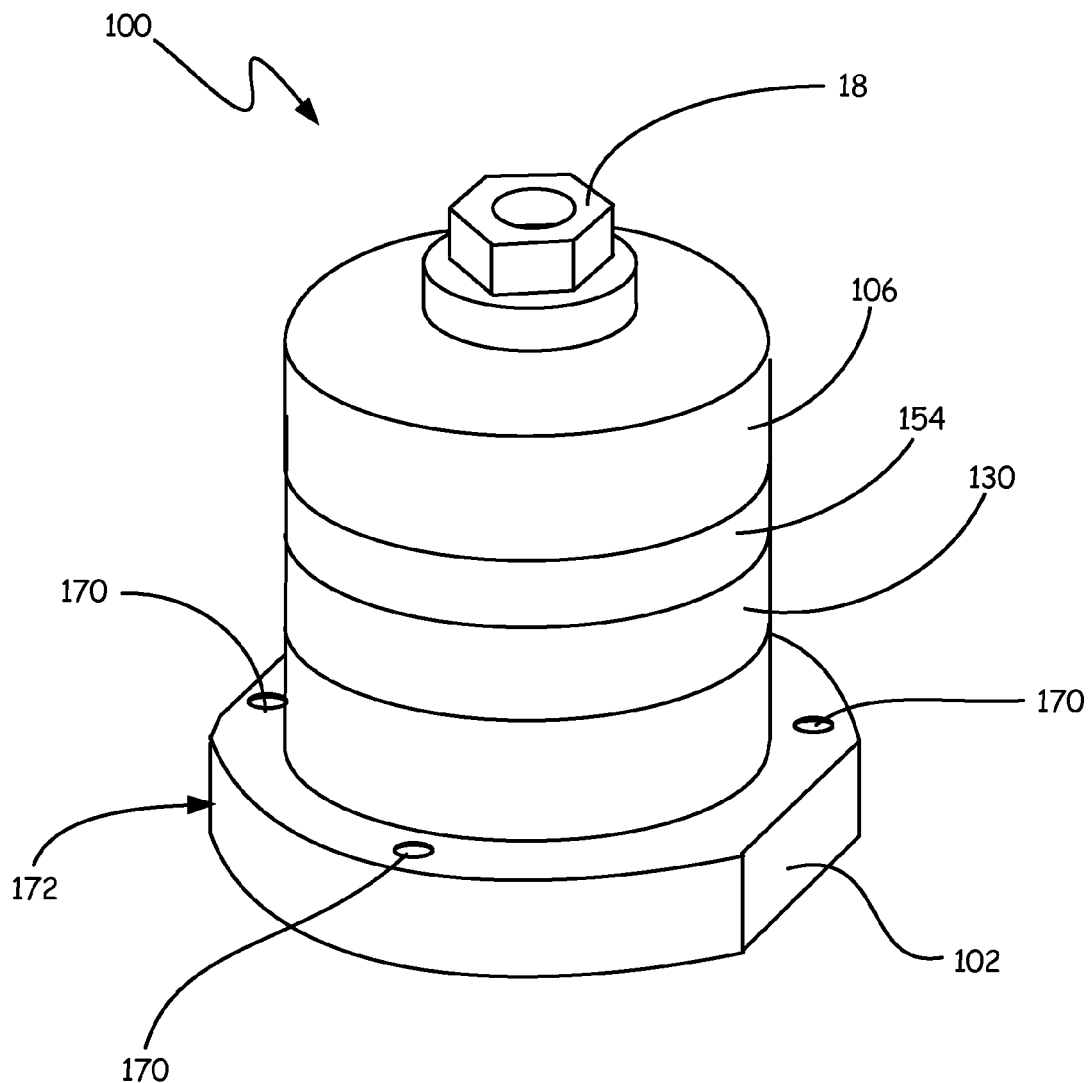
FIG. 4 is a diagrammatic perspective view of a multiport selector valve in accordance with an embodiment of the present invention.

FIG. 4 is a diagrammatic perspective view of a multiport selector valve in accordance with an embodiment of the present invention. Valve 100 is shown in a fully-assembled state. This is so despite the fact that valve 100 is not yet mounted to a gas chromatograph. In order to mount valve 100 to a gas chromatograph, mounting screws or bolts are passed through mounting holes 170 in flange 172. Thus, a fully-assembled valve can be provided to an end user who can perform a simple replacement of a faulty valve without having to disconnect and reconnect multiple threaded tube fittings at the risk of creating leaks or causing mechanical damage to the threads by cross-threading. Over the lifetime of a valve, various situations may be encountered which cause the valve to fail. Due to its unique construction, the valve can be replaced by simply unscrewing the three retaining screws, replacing the valve with an alternate and reattaching it.

Figure 5:
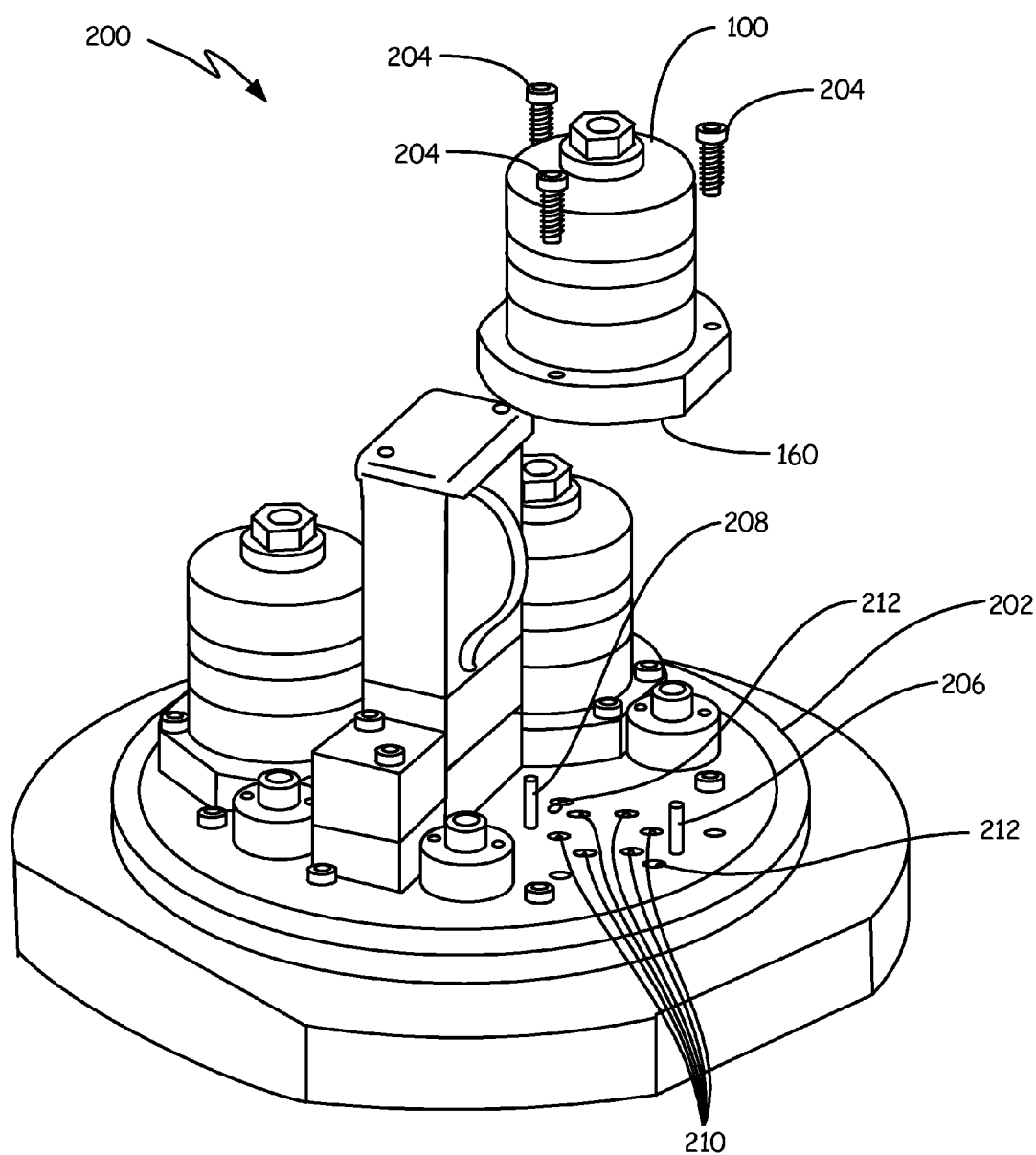
FIG. 5 is a diagrammatic view of a multiport selector valve being mounted to a gas chromatograph in accordance with an embodiment of the present invention.

FIG. 5 is a diagrammatic view of a multiport selector valve being mounted to a gas chromatograph in accordance with an embodiment of the present invention. In the embodiment illustrated in FIG. 5, valve 100 is a six-port valve that is one of three such valves in gas chromatograph 200. Gas chromatograph 200 includes a base 202 having a number of internally-threaded bores configured to mate with mounting screws or bolts 204. A pair of guide pins 206, 208, different than guide pins 144, 146, is placed within plate 202 in order to ensure proper placement of valve 100 as it is mounted to plate 202. Plate 202 also includes ports 210 which are disposed to mate with corresponding apertures in surface 160 of valve 100. O-rings or other suitable structures are provided between plate 202 and surface 160 in order to ensure a leak-tight coupling. However, it is expressly contemplated that a single seal or gasket could be provided for such couplings in accordance with embodiments of the present invention. Actuation gas fluid ports 212 are also fluidically coupled to surface 160 of valve 100. In accordance with one embodiment of the present invention, three mounting holes are equally spaced about the perimeter of flange 172, such that the clamping force provided by screws 204 is evenly distributed across surface 106. Additionally, since bolt 18 is no longer used to secure valve 100 to plate 202, the clamping force within valve 100 can be different than the clamping force between surface 160 and plate 202.

Figure 6:
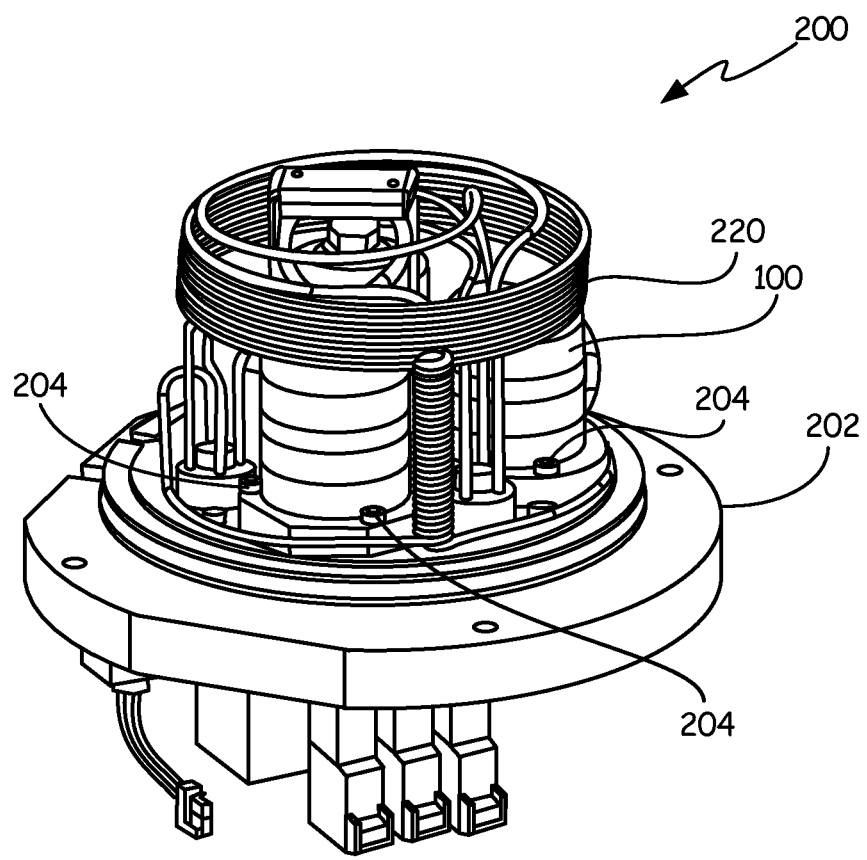
FIG. 6 is a diagrammatic perspective view of a portion of a gas chromatograph employing a plurality of multiport selector valves in accordance with an embodiment of the present invention.

FIG. 6 is a diagrammatic perspective view of a portion of a gas chromatograph employing a plurality of multiport selector valves in accordance with an embodiment of the present invention. The gas chromatograph illustrated in FIG. 6 includes a plurality of columns 220 and associated tubing connections. However, using multiport selector valves in accordance with embodiments of the present invention provides a much simpler assembly in terms of tubing connections and routes in comparison to prior art techniques.

Embodiments of the present invention deviate from prior approaches in the manner in which the gasses are brought into and out of the valve.

Although the present invention has been described with reference to preferred embodiments, workers skilled in the art will recognize that changes may be made in form and detail without departing from the spirit and scope of the invention.

What is claimed is:

1. A pneumatic multiport selector valve comprising:
   a base having a mounting surface configured to mount to an analytic instrument, the mounting surface having a plurality of apertures therein for coupling to flow conduits of the analytic instrument, wherein the base includes a flange having a plurality of mounting holes therethrough;
   at least one piston plate having a number of apertures therethrough;
   a set of pistons slidably disposed in respective apertures of the at least one piston plate;
   a cushion layer disposed between the at least one piston plate and the base, the cushion layer having a plurality of apertures to allow actuation gas therethrough; and
   a plate clamping the at least one piston plate to the base.

2. The pneumatic multiport selector valve of claim 1, and wherein the cushion layer is isolated from the actuation gas.

3. The pneumatic multiport selector valve of claim 2, wherein the cushion layer is porous.

4. The pneumatic multiport selector valve of claim 3, wherein the cushion layer is formed of a meta-aramid material.

5. The pneumatic multiport selector valve of claim 3, and further comprising a plurality of seals isolating the cushion layer from the actuation gas.

6. The pneumatic multiport selector valve of claim 1, wherein the plate is urged toward the base by a threaded member engaged with the base.

7. The pneumatic multiport selector valve of claim 6, wherein the threaded member is a bolt having threads engaged within the base.

8. The pneumatic multiport selector valve of claim 6, wherein the threaded member is torqued to a specified amount.

9. The pneumatic multiport selector valve of claim 1, wherein the mounting holes are evenly distributed about a periphery of the flange to facilitate even sealing force to the mounting surface.

10. The pneumatic multiport valve of claim 1, wherein the mounting surface is substantially planar and wherein fluidic connections for all ports and actuation gas couplings are performed simultaneously.

11. The pneumatic multiport valve of claim 1, wherein the mounting surface has a plurality of bores therein, the plurality of bore being configured to receive alignment pins of an analytic instrument.

12. An analytic instrument comprising:
   a base plate having a plurality of fluid flow apertures arranged thereon;
   a pneumatic multiport selector valve, having:
      a base having a mounting surface mounted to the base plate, the mounting surface having a plurality of apertures therein coupled to respective fluid flow apertures of the base plate;
      a flange comprising a plurality of mounting holes, with threaded connector passing through each respective mounting hole to engage with the base:
      at least one piston plate having a number of apertures therethrough;
      a set of pistons slidably disposed in respective apertures of the at least one piston plate;
      a cushion layer disposed between the at least one piston plate and the base, the cushion layer having a plurality of apertures to allow actuation gas therethrough; and
      a plate clamping the at least one piston plate to the base.

13. The analytic instrument of claim 12, wherein the plate is urged toward the base by a threaded member engaged with the base.

14. The analytic instrument of claim 13, wherein the threaded member is a bolt passing through the center of the plate and being threaded into the base of the multiport selector valve.

15. The analytic instrument of claim 12, wherein an o-ring couples each aperture of the base of the multiport selector valve to a respective aperture of the base plate of the analytic instrument.

* * * * *